United States Patent
Hendriksen et al.

(10) Patent No.: US 8,167,901 B2
(45) Date of Patent: May 1, 2012

(54) REMOVABLE VENA CAVA FILTER COMPRISING STRUTS HAVING AXIAL BENDS

(75) Inventors: Per Hendriksen, Herlufmagle (DK);
Allan G. Hemmingsen, Jystrup (DK);
Arne Molgaard-Nielsen, Oesterbro (DK); Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 311 days.

(21) Appl. No.: 11/235,801

(22) Filed: Sep. 27, 2005

(65) Prior Publication Data

US 2006/0069406 A1 Mar. 30, 2006

Related U.S. Application Data

(60) Provisional application No. 60/613,963, filed on Sep. 27, 2004.

(51) Int. Cl.
*A61M 29/00* (2006.01)
(52) U.S. Cl. .................................... 606/200; 606/127
(58) Field of Classification Search .............. 606/200, 606/191, 192, 194, 195, 198, 113, 114, 127, 606/159; 623/1.1
See application file for complete search history.

(56) References Cited

U.S. PATENT DOCUMENTS

| | | | |
|---|---|---|---|
| 2,281,448 A | 4/1942 | Mathey | |
| 3,137,298 A | 6/1964 | Glassman | |
| 3,174,851 A | 3/1965 | Buehler | |
| 3,334,629 A | 8/1967 | Cohn | |
| 3,540,431 A | 11/1970 | Mobin-Uddin | |
| 3,868,956 A | 3/1975 | Alfidi et al. | |
| 3,952,747 A | 4/1976 | Kimmell, Jr. | |
| 4,425,908 A | 1/1984 | Simon | |
| 4,494,531 A | 1/1985 | Gianturco | |
| 4,619,246 A | 10/1986 | Molgaard-Nielsen et al. | |
| 4,643,184 A | 2/1987 | Mobin-Uddin | |
| 4,655,771 A | 4/1987 | Wallsten | |
| 4,665,906 A | 5/1987 | Jervis | |
| 4,688,553 A | 8/1987 | Metals | |
| 4,727,873 A | 3/1988 | Mobin-Uddin | |
| 4,759,757 A | 7/1988 | Pinchuk | |

(Continued)

FOREIGN PATENT DOCUMENTS

DE 003417738 11/1985

(Continued)

OTHER PUBLICATIONS

International Search Report—PCT/US2005/013322 (Sep. 23, 2005).

(Continued)

*Primary Examiner* — Darwin Erezo
*Assistant Examiner* — Jing Ou
(74) *Attorney, Agent, or Firm* — Brinks Hofer Gilson & Lione

(57) ABSTRACT

A removable vena cava filter configured for simplified delivery to and retrieval from the vena cava of a patient is disclosed. The filter includes struts configured to be arranged in consistent orientation together between expanded (opened) and collapsed (closed) configurations, thereby minimizing entanglement of the struts. Each of the struts has a circumferential bend relative to the longitudinal axis of the filter. The circumferential bends allow for consistent orientation of the struts when moved between the expanded and collapsed configurations and when placed in the closed configuration of the filter.

13 Claims, 4 Drawing Sheets

U.S. PATENT DOCUMENTS

| | | | |
|---|---|---|---|
| 4,781,177 A | 11/1988 | Lebigot | |
| 4,793,348 A | 12/1988 | Palmaz | |
| 4,817,600 A | 4/1989 | Herms et al. | |
| 4,830,003 A | 5/1989 | Wolff et al. | |
| 4,832,055 A | 5/1989 | Palestrant | |
| 4,856,516 A | 8/1989 | Hillstead | |
| 4,873,978 A | 10/1989 | Ginsburg | |
| 4,943,297 A | 7/1990 | Saveliev et al. | |
| 4,950,227 A | 8/1990 | Savin et al. | |
| 4,954,126 A | 9/1990 | Wallsten | |
| 4,957,501 A | 9/1990 | Lahille et al. | |
| 4,969,891 A | 11/1990 | Gewertz | |
| 4,990,156 A | 2/1991 | Lefebvre | |
| 5,037,377 A | 8/1991 | Alonso | |
| 5,059,205 A | 10/1991 | El-Nounou et al. | |
| 5,061,275 A | 10/1991 | Wallsten et al. | |
| 5,067,957 A | 11/1991 | Jervis | |
| 5,071,407 A | 12/1991 | Termin et al. | |
| 5,108,418 A | 4/1992 | Lefebvre | |
| 5,108,419 A | 4/1992 | Reger et al. | |
| 5,133,733 A | 7/1992 | Rasmussen et al. | |
| 5,135,516 A | 8/1992 | Sahatjian et al. | |
| 5,147,379 A | 9/1992 | Sabbaghian et al. | |
| 5,152,777 A | 10/1992 | Goldberg et al. | |
| 5,160,342 A | 11/1992 | Reger et al. | |
| 5,190,546 A | 3/1993 | Jervis | |
| 5,217,484 A | 6/1993 | Marks | |
| 5,221,261 A | 6/1993 | Termin et al. | |
| 5,224,953 A | 7/1993 | Morgentaler | |
| 5,234,458 A | 8/1993 | Metais | |
| 5,242,462 A | 9/1993 | El-Nounou et al. | |
| 5,300,086 A | 4/1994 | Gory et al. | |
| 5,304,121 A | 4/1994 | Sahatjian | |
| 5,304,200 A | 4/1994 | Spaulding | |
| 5,324,304 A | 6/1994 | Rasmussen | |
| 5,329,942 A | 7/1994 | Gunther et al. | |
| 5,344,427 A | 9/1994 | Cottenceau et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,382,261 A | 1/1995 | Palmaz | |
| 5,383,887 A | 1/1995 | Nadal | |
| 5,405,377 A | 4/1995 | Cragg | |
| 5,413,586 A | 5/1995 | Dibie et al. | |
| 5,421,832 A | 6/1995 | Lefebvre | |
| 5,476,508 A | 12/1995 | Amstrup | |
| 5,527,338 A | 6/1996 | Purdy | |
| 5,540,712 A | 7/1996 | Kleshinski et al. | |
| 5,549,626 A | 8/1996 | Miller et al. | |
| 5,549,629 A | 8/1996 | Thomas et al. | |
| 5,601,595 A | 2/1997 | Smith | |
| 5,626,605 A | 5/1997 | Irie et al. | |
| 5,630,801 A | 5/1997 | Roussigne et al. | |
| 5,634,942 A | 6/1997 | Chevillon et al. | |
| 5,649,906 A * | 7/1997 | Gory et al. | 606/108 |
| 5,649,953 A | 7/1997 | Lefebvre | |
| 5,669,933 A | 9/1997 | Simon et al. | |
| 5,681,347 A | 10/1997 | Cathcart et al. | |
| 5,683,411 A | 11/1997 | Kavteladze et al. | |
| 5,695,519 A | 12/1997 | Summers et al. | |
| 5,709,704 A | 1/1998 | Nott et al. | |
| 5,720,764 A | 2/1998 | Naderlinger | |
| 5,725,550 A | 3/1998 | Nadal | |
| 5,746,767 A | 5/1998 | Smith | |
| 5,755,778 A | 5/1998 | Kleshinski | |
| 5,755,790 A | 5/1998 | Chevillon et al. | |
| 5,776,162 A | 7/1998 | Kleshinski | |
| 5,800,457 A | 9/1998 | Gelbfish | |
| 5,800,525 A | 9/1998 | Bachinski et al. | |
| 5,807,398 A | 9/1998 | Shaknovich | |
| 5,810,874 A | 9/1998 | Lefebvre | |
| 5,836,968 A | 11/1998 | Simon et al. | |
| 5,836,969 A | 11/1998 | Kim et al. | |
| 5,843,244 A | 12/1998 | Pelton et al. | |
| 5,853,420 A | 12/1998 | Chevillon et al. | |
| 5,895,399 A | 4/1999 | Barbut et al. | |
| 5,902,317 A | 5/1999 | Kleshinski et al. | |
| 5,916,235 A | 6/1999 | Guglielmi | |
| 5,928,260 A | 7/1999 | Chin et al. | |
| 5,928,261 A | 7/1999 | Ruiz | |
| 5,932,035 A | 8/1999 | Koger et al. | |
| 5,938,683 A | 8/1999 | Lefebvre | |
| 5,951,585 A | 9/1999 | Cathcart et al. | |
| 5,961,546 A | 10/1999 | Robinson et al. | |
| 5,976,172 A | 11/1999 | Homsma et al. | |
| 5,984,947 A | 11/1999 | Smith | |
| 6,007,557 A | 12/1999 | Ambrisco et al. | |
| 6,007,558 A | 12/1999 | Ravenscroft et al. | |
| 6,013,093 A | 1/2000 | Nott et al. | |
| 6,077,274 A | 6/2000 | Ouchi et al. | |
| 6,080,178 A | 6/2000 | Meglin | |
| 6,086,610 A | 7/2000 | Duerig et al. | |
| 6,126,673 A | 10/2000 | Kim et al. | |
| 6,129,755 A | 10/2000 | Mathis et al. | |
| 6,146,404 A | 11/2000 | Kim et al. | |
| 6,152,144 A | 11/2000 | Lesh et al. | |
| 6,156,055 A | 12/2000 | Ravenscroft | |
| 6,156,061 A | 12/2000 | Wallace et al. | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,193,739 B1 | 2/2001 | Chevillon et al. | |
| 6,221,102 B1 | 4/2001 | Baker et al. | |
| 6,231,589 B1 | 5/2001 | Wessman et al. | |
| 6,241,738 B1 | 6/2001 | Dereume | |
| 6,241,746 B1 | 6/2001 | Bosma et al. | |
| 6,245,012 B1 | 6/2001 | Kleshinski | |
| 6,245,088 B1 | 6/2001 | Lowery | |
| 6,251,122 B1 | 6/2001 | Tsukernik | |
| 6,258,026 B1 | 7/2001 | Ravenscroft et al. | |
| 6,267,776 B1 | 7/2001 | O'Connell | |
| 6,273,900 B1 | 8/2001 | Nott et al. | |
| 6,273,901 B1 | 8/2001 | Whitcher et al. | |
| 6,277,139 B1 | 8/2001 | Levinson et al. | |
| 6,287,315 B1 | 9/2001 | Wijeratne et al. | |
| 6,287,329 B1 | 9/2001 | Duerig et al. | |
| 6,306,163 B1 | 10/2001 | Fitz | |
| 6,312,454 B1 | 11/2001 | Stockel et al. | |
| 6,312,455 B2 | 11/2001 | Duerig et al. | |
| 6,325,815 B1 | 12/2001 | Kusleika et al. | |
| 6,331,183 B1 | 12/2001 | Suon | |
| 6,342,062 B1 | 1/2002 | Suon et al. | |
| 6,342,063 B1 | 1/2002 | DeVries et al. | |
| 6,342,067 B1 | 1/2002 | Mathis et al. | |
| 6,346,116 B1 | 2/2002 | Brooks et al. | |
| 6,364,895 B1 | 4/2002 | Greenhalgh | |
| 6,368,338 B1 | 4/2002 | Konya et al. | |
| 6,391,044 B1 | 5/2002 | Yadav et al. | |
| 6,391,045 B1 | 5/2002 | Kim et al. | |
| 6,436,120 B1 | 8/2002 | Meglin | |
| 6,436,121 B1 | 8/2002 | Blom | |
| 6,447,530 B1 | 9/2002 | Ostrovsky et al. | |
| 6,461,370 B1 | 10/2002 | Gray et al. | |
| 6,468,290 B1 | 10/2002 | Weldon et al. | |
| 6,482,222 B1 | 11/2002 | Bruckheimer et al. | |
| 6,485,502 B2 | 11/2002 | DonMichael et al. | |
| 6,506,205 B2 | 1/2003 | Goldberg et al. | |
| 6,511,503 B1 | 1/2003 | Burkett et al. | |
| 6,517,559 B1 | 2/2003 | O'Connell | |
| 6,527,962 B1 | 3/2003 | Nadal | |
| 6,540,767 B1 | 4/2003 | Walak et al. | |
| 6,551,342 B1 | 4/2003 | Shen et al. | |
| 6,558,404 B2 | 5/2003 | Tsukernik | |
| 6,569,183 B1 | 5/2003 | Kim et al. | |
| 6,579,303 B2 | 6/2003 | Amplatz | |
| 6,582,447 B1 | 6/2003 | Patel et al. | |
| 6,589,266 B2 | 7/2003 | Whitcher et al. | |
| 6,602,226 B1 | 8/2003 | Smith et al. | |
| 6,616,680 B1 | 9/2003 | Thielen | |
| 6,638,294 B1 | 10/2003 | Palmer | |
| 6,652,548 B2 * | 11/2003 | Evans et al. | 606/159 |
| 6,652,558 B2 | 11/2003 | Patel et al. | |
| 6,685,722 B1 | 2/2004 | Rosenbluth et al. | |
| 6,726,621 B2 | 4/2004 | Suon et al. | |
| 6,945,977 B2 * | 9/2005 | Demarais et al. | 606/128 |
| 7,211,089 B2 * | 5/2007 | Kear et al | 606/127 |
| 7,279,000 B2 * | 10/2007 | Cartier et al. | 606/200 |

| | | |
|---|---|---|
| 7,314,477 B1 | 1/2008 | Ravenscroft et al. |
| 7,338,512 B2 | 3/2008 | McGuckin et al. |
| 7,763,045 B2 * | 7/2010 | Osborne ............ 606/200 |
| 2001/0000799 A1 | 5/2001 | Wessman et al. |
| 2001/0011181 A1 | 8/2001 | DiMatteo |
| 2001/0023358 A1 | 9/2001 | Tsukernik |
| 2001/0034547 A1 | 10/2001 | Hall et al. |
| 2001/0034548 A1 | 10/2001 | Vrba et al. |
| 2001/0037126 A1 | 11/2001 | Stack et al. |
| 2001/0039432 A1 | 11/2001 | Whitcher et al. |
| 2002/0002401 A1 | 1/2002 | McGuckin, Jr. et al. |
| 2002/0016624 A1 | 2/2002 | Patterson et al. |
| 2002/0032460 A1 | 3/2002 | Kusleika et al. |
| 2002/0039445 A1 | 4/2002 | Abe et al. |
| 2002/0055767 A1 | 5/2002 | Forde et al. |
| 2002/0087187 A1 | 7/2002 | Mazzocchi et al. |
| 2002/0099431 A1 | 7/2002 | Armstrong et al. |
| 2002/0116024 A1 | 8/2002 | Goldberg et al. |
| 2002/0133217 A1 | 9/2002 | Sirhan et al. |
| 2002/0138097 A1 | 9/2002 | Ostrovsky et al. |
| 2002/0156520 A1 | 10/2002 | Boylan et al. |
| 2002/0161393 A1 | 10/2002 | Demond et al. |
| 2002/0169474 A1 | 11/2002 | Kusleika et al. |
| 2002/0169495 A1 | 11/2002 | Gifford et al. |
| 2002/0183782 A1 | 12/2002 | Tsugita et al. |
| 2002/0193827 A1 | 12/2002 | McGuckin, Jr. et al. |
| 2002/0193828 A1 | 12/2002 | Griffin et al. |
| 2002/0193874 A1 | 12/2002 | Crowley |
| 2003/0018343 A1 | 1/2003 | Mathis |
| 2003/0028238 A1 | 2/2003 | Burkett et al. |
| 2003/0040772 A1 | 2/2003 | Hyodoh et al. |
| 2003/0055481 A1 | 3/2003 | McMorrow |
| 2003/0069596 A1 | 4/2003 | Eskuri |
| 2003/0074019 A1 | 4/2003 | Gray et al. |
| 2003/0078614 A1 | 4/2003 | Salahieh et al. |
| 2003/0083692 A1 | 5/2003 | Vrba et al. |
| 2003/0097145 A1 | 5/2003 | Goldberg et al. |
| 2003/0105484 A1 | 6/2003 | Boyle et al. |
| 2003/0109897 A1 | 6/2003 | Walak et al. |
| 2003/0114880 A1 | 6/2003 | Hansen et al. |
| 2003/0125790 A1 | 7/2003 | Fastovsky et al. |
| 2003/0125793 A1 | 7/2003 | Vesely |
| 2003/0130681 A1 | 7/2003 | Ungs |
| 2003/0144686 A1 | 7/2003 | Martinez et al. |
| 2003/0153943 A1 | 8/2003 | Michael et al. |
| 2003/0153945 A1 | 8/2003 | Patel et al. |
| 2003/0163159 A1 | 8/2003 | Patel et al. |
| 2003/0176888 A1 * | 9/2003 | O'Connell ............ 606/200 |
| 2003/0181922 A1 | 9/2003 | Alferness |
| 2004/0010282 A1 | 1/2004 | Kusleika |
| 2004/0158273 A1 | 8/2004 | Weaver et al. |
| 2004/0186510 A1 | 9/2004 | Weaver |
| 2004/0193209 A1 | 9/2004 | Pavcnik et al. |
| 2004/0230220 A1 | 11/2004 | Osborne |
| 2005/0107822 A1 | 5/2005 | WasDyke |
| 2005/0165441 A1 | 7/2005 | McGuckin, Jr. et al. |
| 2005/0165442 A1 | 7/2005 | Thinnes, Jr. et al. |
| 2005/0251199 A1 | 11/2005 | Osborne et al. |
| 2005/0267512 A1 | 12/2005 | Osborne et al. |
| 2005/0267513 A1 | 12/2005 | Osborne et al. |
| 2005/0267514 A1 | 12/2005 | Osborne et al. |
| 2006/0100660 A1 | 5/2006 | Osborne et al. |
| 2007/0005095 A1 | 1/2007 | Osborne et al. |

FOREIGN PATENT DOCUMENTS

| | | |
|---|---|---|
| DE | 3429850 A1 | 2/1986 |
| EP | 0270432 A1 | 6/1988 |
| EP | 0348295 A1 | 12/1989 |
| EP | 0350043 A1 | 10/1990 |
| EP | 0430848 A1 | 6/1991 |
| EP | 0437121 A2 | 7/1991 |
| EP | 0462008 A1 | 12/1991 |
| EP | 0472334 A1 | 2/1992 |
| EP | 0701800 A1 | 3/1996 |
| FR | 2587901 | 4/1987 |
| FR | 2649884 | 1/1991 |
| FR | 2672487 | 8/1992 |
| GB | 2200848 A | 8/1988 |
| GB | 2200848 B | 8/1988 |
| SU | 835447 | 6/1981 |
| SU | 1103868 A | 7/1984 |
| SU | 955912 A | 2/1988 |
| WO | WO 91/04716 | 4/1991 |
| WO | WO 91/11972 | 8/1991 |
| WO | WO 95/08567 | 3/1995 |
| WO | WO 95/27448 | 10/1995 |
| WO | WO 96/17634 | 6/1996 |
| WO | WO 01/06952 A1 | 2/2001 |
| WO | WO 03/011188 A1 | 2/2003 |
| WO | WO 2004/049973 A1 | 6/2004 |
| WO | WO 2005/072645 A1 | 8/2005 |
| WO | WO2005/102210 A1 | 11/2005 |
| WO | WO2005/102211 A1 | 11/2005 |
| WO | WO2005/102212 A1 | 11/2005 |
| WO | WO2005/102213 A1 | 11/2005 |
| WO | WO2005/102214 A1 | 11/2005 |
| WO | WO2006/036867 A1 | 4/2006 |

OTHER PUBLICATIONS

International Search Report—PCT/US2005/013323 (Sep. 23, 2005).
International Search Report—PCT/US2005/013158 (Oct. 7, 2005).
International Search Report—PCT/US2005/013281 (Oct. 7, 2005).
International Search Report—PCT/US2005/013160) Sep. 22, 2005).
International Search Report—PCT/US2005/034350 (Feb. 10, 2006).
Morris Simon, M.D. et al., A Vena Cava Filter Using Thermal Shape Memory Alloy, Oct. 1977, 89-94.
James Hansen, Metal That Remember, 44-47, Jun. 1981.
Morris Simon et al., Transvenous Devices for the Management of Pulmonary Embolism, 1980, 112-121.
J.L. Kraimps et al., Annals of Vascular Surgery, Mar. 1992, 99-110.
Jean-Louis Kraimps, M.D. et al., Optimal Central Trapping (OPCETRA) Vena Cava Filter: Results of Experimental Studies, Nov. 1992, 697-699.

* cited by examiner

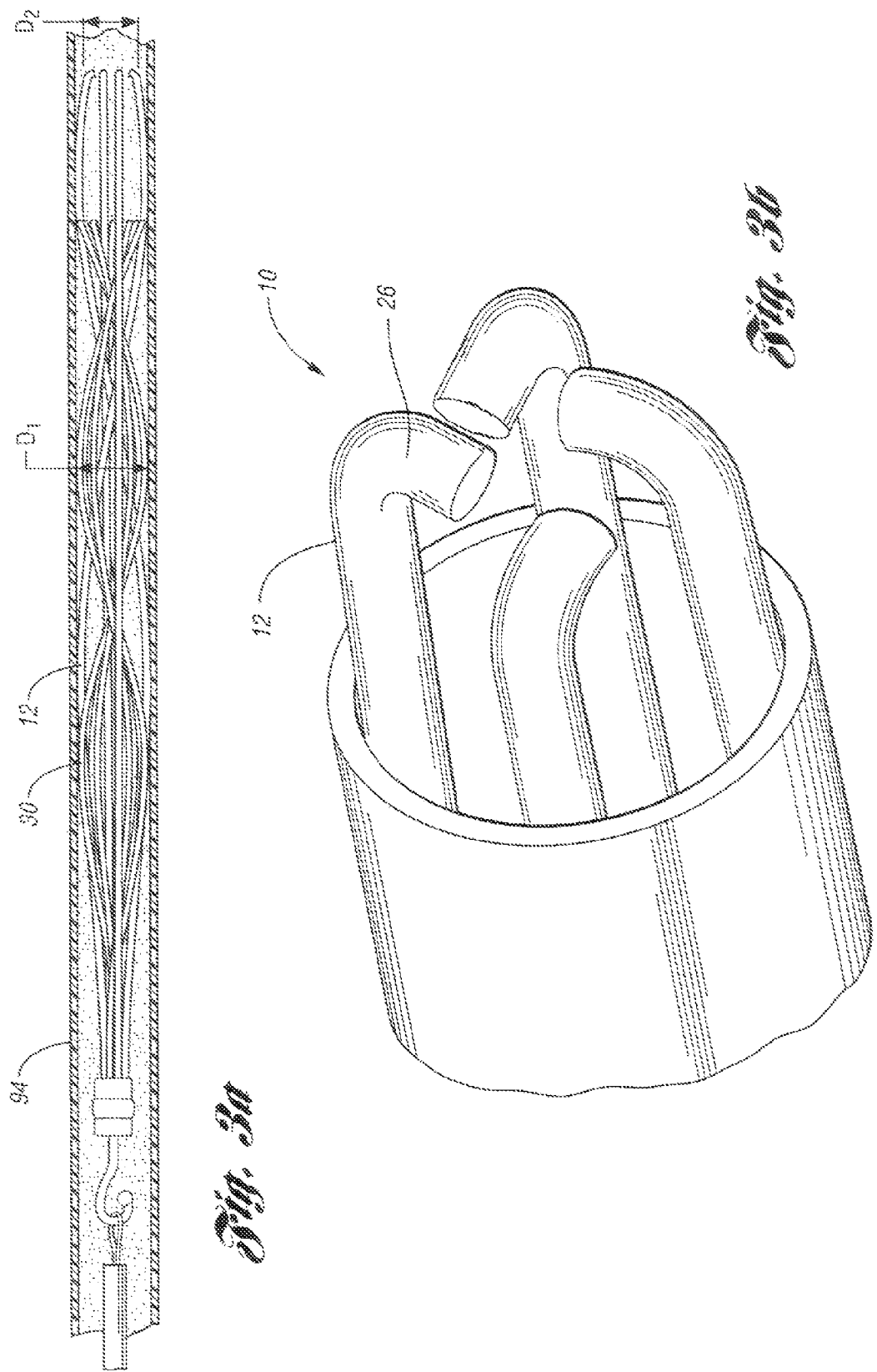

REMOVABLE VENA CAVA FILTER COMPRISING STRUTS HAVING AXIAL BENDS

CROSS-REFERENCE TO RELATED APPLICATIONS

This application claims the benefit of U.S. Provisional Application Ser. No. 60/613,963, filed on Sep. 27, 2004, entitled "REMOVABLE VENA CAVA FILTER HAVING STRUTS LONGITUDINALLY ANGLED FOR CONSISTENT ORIENTATION IN COLLAPSED CONFIGURATION," the entire contents of which are incorporated herein by reference.

BACKGROUND OF THE INVENTION

The present invention relates to medical devices. More particularly, the invention relates to a removable vena cava clot filter that can be percutaneously placed in and removed from the vena cava of a patient.

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

The benefits of a vena cava filter have been well established, but improvements may be made. For example, filters generally may be configured to be self-expandable when they are deployed in the vena cava of a patient. Struts of a vena cava filter may be configured to move radially between an expanded state for engaging the walls of the vena cava and a collapsed state for filter delivery and retrieval. In the collapsed state, struts of the filter may be randomly housed within a delivery sheath. While moving between the expanded and collapsed states, the strut ends may cross over each other in random fashion causing a risk of entanglement. Entanglement during filter deployment may undesirably increase time duration of the procedure.

BRIEF SUMMARY OF THE INVENTION

The present invention generally provides a removable vena cava filter configured for simplified delivery to and retrieval from the vena cava of a patient. The filter is shaped such that its struts may be arranged in consistent orientation together between expanded (opened) and collapsed (closed) configurations, thereby minimizing entanglement of the struts. The filter includes primary struts, each having an axial bend relative to the longitudinal axis of the filter. The axial bends allow for consistent orientation of the struts when moved between the expanded and collapsed configurations and when placed in the closed configuration of the filter.

One embodiment of the present invention provides a removable filter for capturing thrombi in a blood vessel. In this embodiment, the filter comprises a plurality of struts having first ends attached together adjacent a center point along a longitudinal axis. Each primary strut has an arcuate segment including a first curved portion and a second curved portion. The first curved portion of each primary strut has an axial bend relative to the longitudinal axis such that the primary struts are arranged in consistent orientation between open and closed states. The axial bends of the primary struts are angled consistently together relative to the longitudinal axis. The first curved portion extends from the first end and the second curved portion extends from the first curved portion and terminates at the anchoring hook. The primary struts are configured to move between the expanded state for engaging with the blood vessel and the collapsed state for filter retrieval or delivery.

In another embodiment, the removable filter comprises a plurality of primary struts having first ends attached together along a longitudinal axis. The primary struts are movable between a closed state during delivery to the blood vessel and an open state when engaged with the blood vessel. Each primary strut generally extends from the first end in a circumferential direction relative to the longitudinal axis and terminates in an anchoring hook. The primary struts are equidistantly arranged about the longitudinal axis in both open and closed states.

Further aspects, features, and advantages of the invention will become apparent from consideration of the following description and the appended claims when taken in connection with the accompanying drawings.

BRIEF DESCRIPTION OF THE DRAWINGS

FIG. 2b is an enlarged view of circle 2b in FIG. 2a;

FIG. 3a is a side view of the vena cava filter of FIG. 2a in a collapsed state and disposed in an introducer tube.

FIG. 3b is an enlarged view of anchoring hooks of the vena cava filter in the collapsed state;

DETAILED DESCRIPTION OF THE INVENTION

Embodiments of the present invention provide a filter for capturing thrombi, wherein struts of the filter are angled for consistent orientation between opened and closed configurations. The features of the filter generally allow for a reduced risk of strut entanglement when the struts move between open and closed configurations. Generally, this is accomplished by maintaining the struts in a continuous consistent orientation. More specifically, this consistent orientation of the struts is provided by an axial or a circumferential bend formed on each strut relative to the longitudinal axis of the filter such that the struts are arranged consistently when moving between the expanded (open) to the collapsed (closed) states of the filter.

The axial bend of each strut solves the concern of entanglement during filter delivery or retrieval. As a result, the axial bends on the struts ensure a more time effective and accurate deployment of the filter in a body vessel of a patient.

Figure 1:
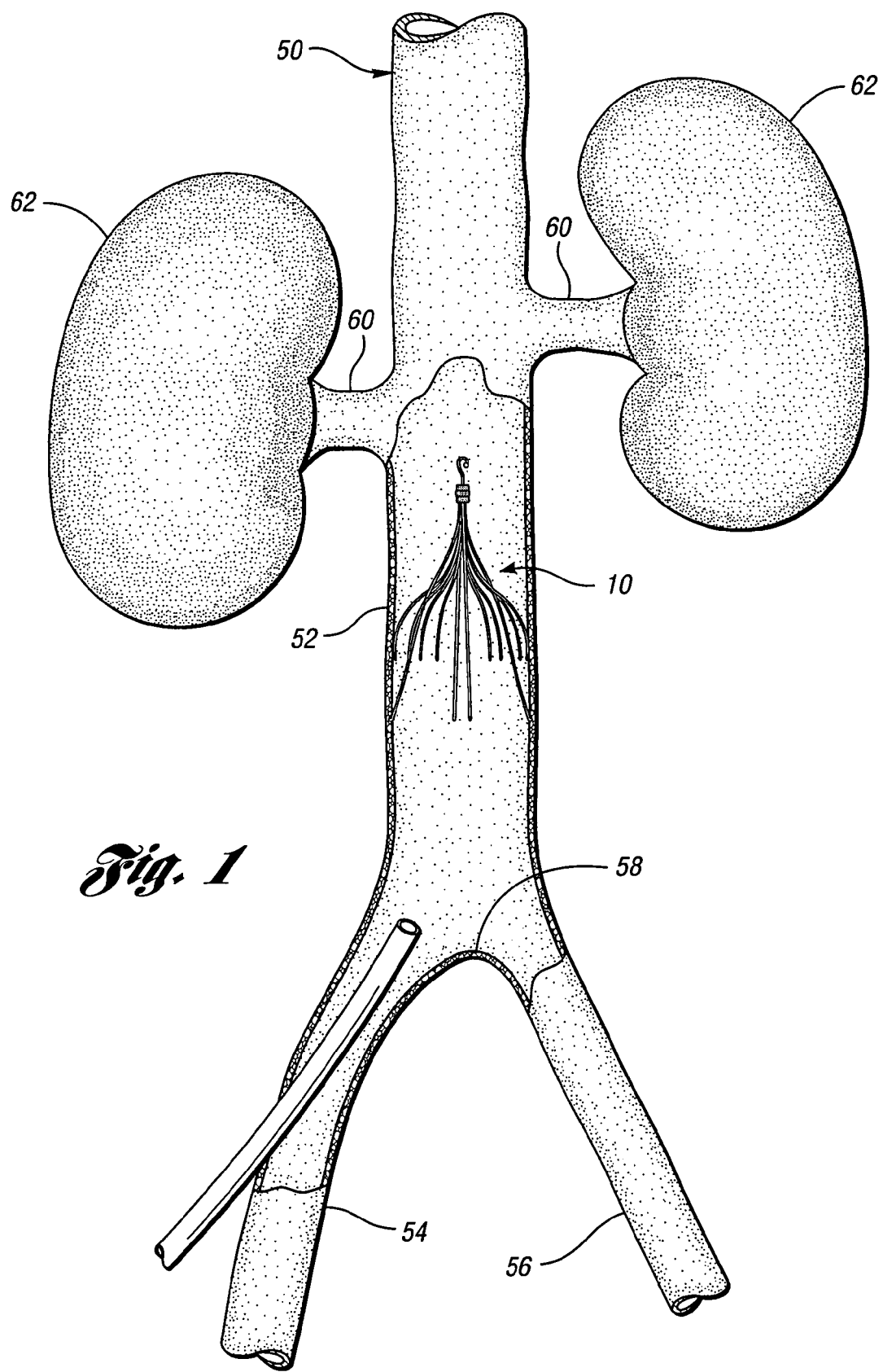
FIG. 1 is an illustration of the anatomy of the renal veins, the iliac veins, and the vena cava in which one embodiment of a vena cava filter of the present invention is deployed.

In accordance with one embodiment of the present invention, FIG. 1 illustrates a vena cava filter 10 implanted in the vena cava 50 for the purpose of lysing or capturing thrombi carried by the blood flowing through the iliac veins 54, 56 toward the heart and into the pulmonary arteries. As shown, the iliac veins 54, 56 merge at juncture 58 into the vena cava 50. The renal veins 60 from the kidneys 62 join the vena cava 50 downstream of juncture 58. The portion of the vena cava 50, between the juncture 58 and the renal veins 60, defines the inferior vena cava 52 in which the vena cava filter 10 has been percutaneously deployed through one of the femoral veins. Preferably, the vena cava filter 10 has a length smaller than the length of the inferior vena cava 52. If the lower part of the filter extends into the iliac veins, filtering effectiveness will be compromised and if the filter wires cross over the origin of the renal veins the filter wires might interfere with the flow of blood from the kidneys.

Figure 2A:
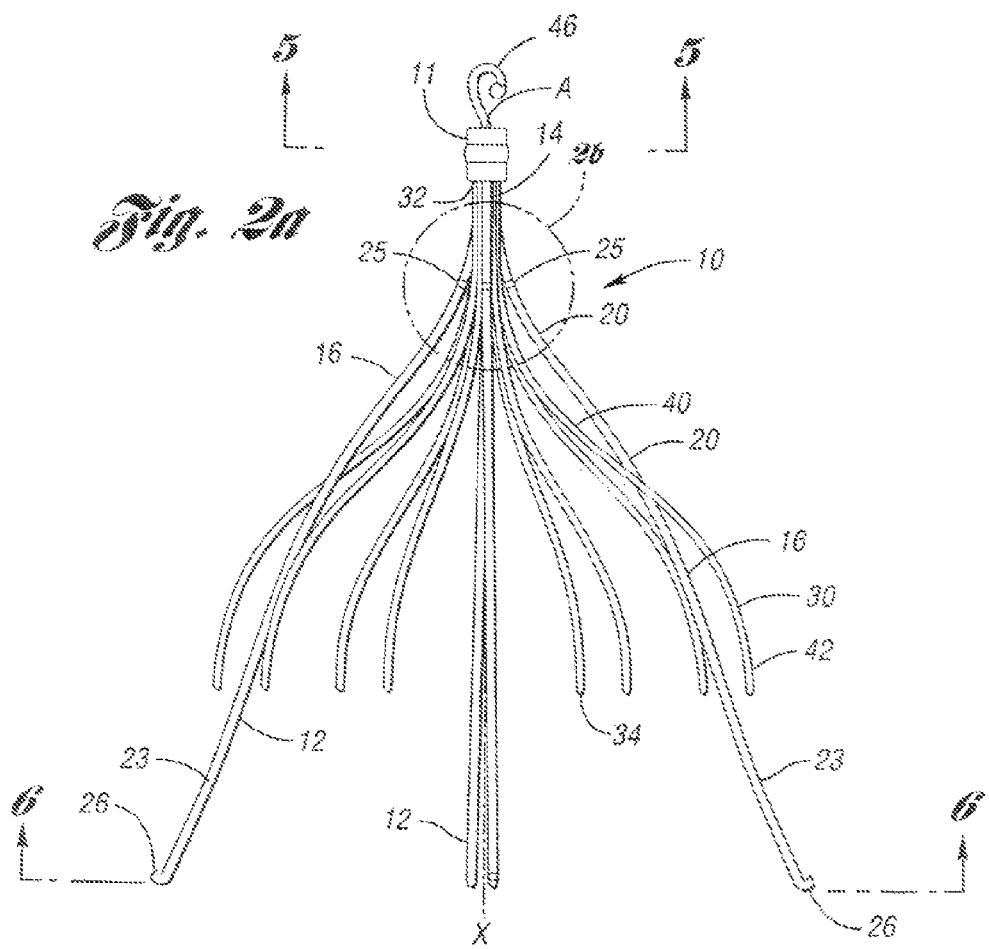
FIG. 2a is a side perspective view of one embodiment of the vena cava filter in an expanded state.

This embodiment of the present invention will be further discussed with reference to FIGS. 2a to 6 in which filter 10 is shown. FIG. 2a illustrates filter 10 in an expanded state and comprising four primary struts 12 each having first ends that emanate from a hub 11. Hub 11 attaches by crimping first ends 14 of primary struts 12 together along a center point A in a compact bundle along a central or longitudinal axis X of the filter. The hub 11 has a minimal diameter for the size of wire used to form the struts. Preferably, the primary struts 12 are formed from superelastic material, nitinol, stainless steel wire, cobalt-chromium-nickel-molybdenum-iron alloy, cobalt-chrome alloy, or any other suitable material that will result in a self-opening or self-expanding filter. In this embodiment, the primary struts 12 are preferably formed from wire having a round or near round cross-section with a diameter of at least about 0.015 inches. Of course, it is not necessary that the primary struts have a round cross-section. For example, the primary struts 12 could take on any shape with rounded edges to maintain non-turbulent blood flow.

As shown in FIG. 2a, each primary strut 12 includes an arcuate segment 16 having a soft S-shape. Each arcuate segment 16 is formed with a first curved portion 20 that is configured to softly bend away from the longitudinal or central axis X of the filter 10 and a second curved portion 23 that is configured to softly bend toward the longitudinal axis of the filter 10. Due to the soft bends of each arcuate segment 16, a prominence or a point of inflection on the primary strut 12 is substantially avoided to aid in non-traumatically engaging the vessel wall. As explained in more detail below with reference to FIG. 4, a distal bend 43 is formed on each of the struts 12 extending outwardly radially from the longitudinal axis X. The distal bend 43 may have a length of between about 1 and 7 millimeters, preferably between about 2 and 4 millimeters.

Figure 2B:
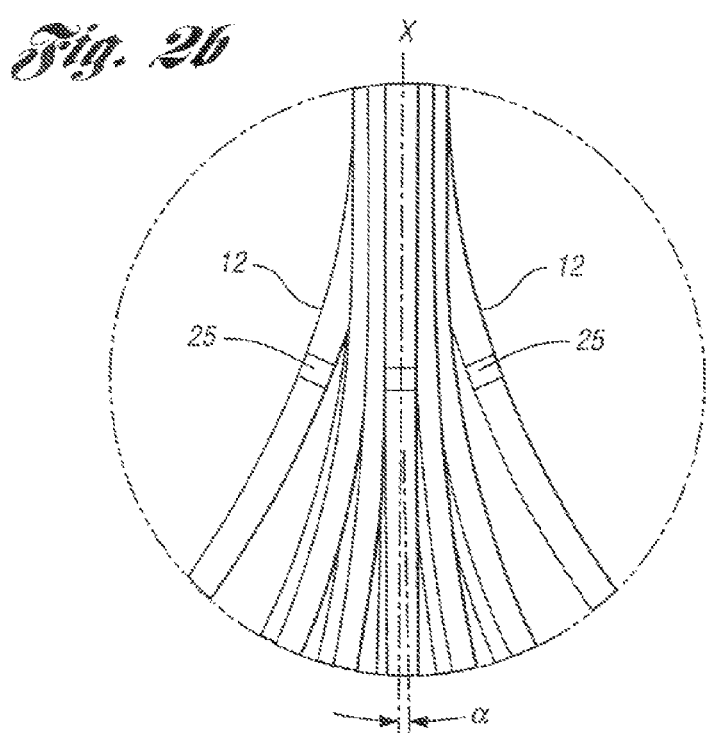

As shown in FIG. 2b, the first curved portion 20 of each primary strut 12 has an axial or a circumferential bend 25. As shown, axial bend 25 on each strut 12 results in each strut 12 being angled from the longitudinal axis X by an angle α. Each curve portion 20 has axial bend 25 formed thereon relative to the longitudinal axis X of filter 10 such that the primary struts 12 maintain continuous consistent orientation together when moving between the opened and closed configurations. Thus, as the filter moves between the opened and closed configuration, the primary struts 12 maintain a relatively uniform or relatively symmetrical arrangement relative to an end view of the filter. The axial bend 25 causes the struts 12 to close and open relatively consistently, lessening the chance of entanglement. For example (see end view in FIG. 6), the relative arrangement of the struts 12 is maintained, avoiding crossing over of struts and thus lessening entanglement thereof.

The axial bends 25 cause the primary struts 12 to be consistently oriented together relative to the longitudinal axis X in each occasion the filter is collapsed in the closed state. Thus, when the filter is loaded in its collapsed configuration and deployed in a body vessel to its expanded configuration, the struts expand consistently radially outwardly and remain in relatively the same orientation or arrangement together. As a result, the risk of entanglement of the struts is reduced.

The angle of each axial bend 25 may range between about 0.5 and 5°. As the primary struts 12 move between the closed state and the expanded state of the filter, the second curved portions 23 move consistently radially, in a rotating fashion, from the longitudinal axis toward the vessel wall. The rotating radial movement of the second curved portions 23 aid in reducing the risk of entanglement of the struts 12.

As shown in FIG. 2a, the primary struts 12 terminate at anchoring hooks 26 that will anchor in the vessel wall when the filter 10 is deployed at a delivery location in the blood vessel. The primary struts 12 are configured to move between the expanded state for engaging the anchoring hooks 26 with the blood vessel and the collapsed state for filter retrieval or delivery. In the expanded state, each arcuate segment 16 extends arcuately along the longitudinal plane (see side view in FIG. 2a) from the first end 14 to the anchoring hook 26.

When the filter 10 is deployed in a blood vessel, the anchoring hooks 26 engage the walls of the blood vessel to define a first axial plane to secure the filter in the blood vessel. The anchoring hooks 26 prevent the filter 10 from migrating from the delivery location in the blood vessel where it has been deposited. The primary struts 12 are shaped and dimensioned such that, when the filter 10 freely expanded, the filter 10 has a diameter of between about 25 mm and 45 mm and a length of between about 3 cm and 7 cm. For example, the filter 10 may have a diameter of about 35 mm and a length of about 5 cm when freely expanded. The primary struts 12 have sufficient spring strength that when the filter is deployed the anchoring hooks 26 will anchor into the vessel wall.

In this embodiment, the filter 10 includes a plurality of secondary struts 30 having connected ends 32 attached that also emanate from hub 11 as shown in FIG. 2a. Hub 11 attaches by crimping the connected ends 32 along the center point A of the secondary struts 30 together with the primary struts 12. In this embodiment, each primary strut 12 has two secondary struts 30 in side-by-side relationship with the primary strut 12. The secondary struts 30 extend from the connected ends 32 to free ends 34 to centralize the filter 10 in the expanded state in the blood vessel. As shown, each secondary strut 30 extends arcuately along a longitudinal plane from the connected end 32 to the free end 34.

The secondary struts 30 may be made from the same type of material as the primary struts 12. However, the secondary struts 30 may have a smaller diameter, e.g., at least about 0.012 inches, than the primary struts 12. In this embodiment, each of the secondary struts 30 is formed of a first arc 40 and a second arc 42. As shown in FIG. 2a, the first arc 40 extends from the connected end 32 away from the longitudinal axis X. The second arc 42 extends from the first arc 40 towards the longitudinal axis X. As shown, two secondary struts 30 are located on each side of one primary strut 12 to form a part of a netting configuration of the filter 10. The hub 11 is preferably made of the same material as the primary struts and secondary struts to minimize the possibility of galvanic corrosion or molecular changes in the material due to welding.

When freely expanded, free ends 34 of the secondary struts 30 will expand radially outwardly to a diameter of about 25 mm to 45 mm. For example, the secondary struts 30 may expand radially outwardly to a diameter of between about 35 mm and 45 mm. The second arcs 42 of the free ends 34 engage the wall of a blood vessel to define a second axial plane where the vessel wall is engaged. The secondary struts 30 function to stabilize the position of the filter 10 about the center of the blood vessel in which it is deployed. As a result, the filter 10 has two layers or planes of struts longitudinally engaging the vessel wall of the blood vessel. The length of the filter 10 is preferably defined by the length of a primary strut 12. As shown, removal hook 46 extends from hub 11 opposite primary and secondary struts 12 and 30.

In this embodiment, each arcuate segment 16 has a thickness of at least about 0.015 inch and a tensile strength of between about 285,000 pounds per square inch (psi) and 330,000 psi. Each anchoring hook 26 is integral with the arcuate segment 16 and has the thickness and the tensile strength of the arcuate segment. Each secondary strut 30 has a thickness of at least about 0.012 inch and a tensile strength of between about 285,000 psi and 330,000 psi.

FIG. 3a illustrates the filter 10 in a collapsed state disposed in a delivery/retrieval tube 94 for delivery or retrieval. As shown, the filter 10 has primary struts 12, each of which is formed with an axial bend for consistent orientation and shaped to cooperate with another primary strut 12 along the longitudinal axis X. As a result, shown in the collapsed state in FIGS. 3a and 3b, the anchoring hooks 26 are configured to be inverted or be inwardly positioned along the longitudinal axis X away from the blood vessel walls for retrieval/delivery of the filter 10. This inverted or inwardly facing configuration of the anchoring hooks 26 allows for simplified delivery and retrieval of filter 10. For example, a concern that the anchoring hooks 26 in the collapsed state may scrape, scratch, or tear the inner wall of a delivery/retrieval tube is eliminated, since the filter 10 of the present invention is shaped to have the anchoring hooks 26 inwardly face toward or positioned adjacent each other and away from the walls of the blood vessel.

A pair of opposed primary struts may be offset by bending each of the struts by the angle α which may be by between about 0.5 degree and 2 degrees at right angles relative to the first end of each strut and the longitudinal axis X of filter 10 to allow the pair of struts to cross each other. In this embodiment, the offset is provided by bending the strut at or near the region between the first and secondary curved sections 20, 23. By the offset, two opposed primary struts 12 may extend substantially in parallel, when seen in the plane of each arcuately extending strut.

Moreover, as shown in FIGS. 3a and 3b in the collapsed state, each primary strut 12 is configured to cooperate with another primary strut 12 along the longitudinal axis X such that the arcuate segments 16, first curved portions 20 or second curved portions 23, occupy a first diameter $D_1$. In this embodiment, the first diameter is greater than a second diameter $D_2$ occupied by the anchoring hooks 26 for filter retrieval or delivery. It has been found that the first diameter of the arcuate segments 16 serves to clear a path of retrieval, reducing radial force from the sheath or blood vessel on the anchoring hooks 26 during removal of the filter 10 from a patient. Reducing the radial force on the anchoring hooks 26 assists in preventing the anchoring hooks 26 from scraping, scratching, or tearing the inner wall of a sheath during removal of the filter 10 from a patient.

In this embodiment of the present invention, it is to be noted that the filter 10 may be delivered or retrieved by any suitable introducer (delivery or retrieval) tube. However, it is preferred that the introducer tube has an inside diameter of between about 4.5 French and 16 French, and more preferably between about 6.5 French and 14 French.

Figure 4:
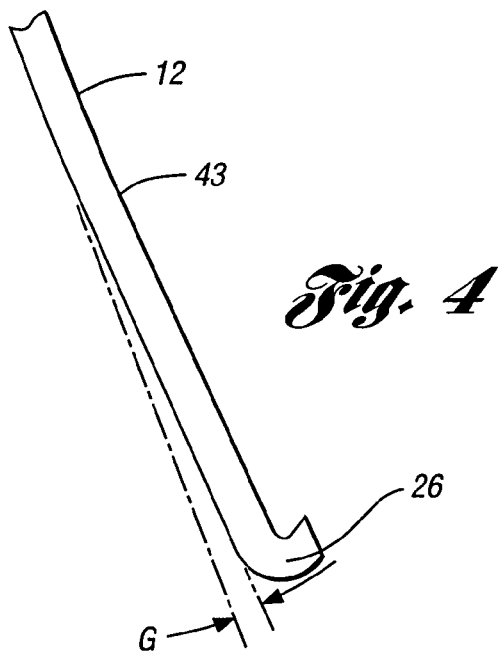
FIG. 4 is an enlarged view a portion of a second arcuate portion of a primary strut of the vena cava filter.

FIG. 4 illustrates primary strut 12 including distal bend 43 formed thereon and extending outwardly radially from the longitudinal axis X. As shown in FIG. 4, the distal bend 43 may extend outwardly at an angle between about 0.5 degree and 2 degrees, preferably 1 degree. The distal bend 43 may be situated at a distance from the anchoring hook 26, which is arranged at the end of a substantially straight strut segment. The distal bend 43 allows the filter 10 to filter thrombi effectively at a smaller inside diameter of a blood vessel than otherwise would be possible while maintaining the ability to collapse for delivery or retrieval. Further, the distal bend 43 provides for a more firm engagement of the anchoring hook 26 at the vessel wall. At the engagement of the anchoring hook 26 with the vessel wall, the primary struts 12 will urge the vessel wall outwards, whereas the vessel wall will urge the primary struts 12 inwards toward the longitudinal axis X of the filter 10. In a preferred embodiment, the anchoring hooks 26 are angled by between about 50 and 80 degrees with respect to the last segment of the primary strut 12, preferably between about 50 and 60 degrees.

Figure 5:
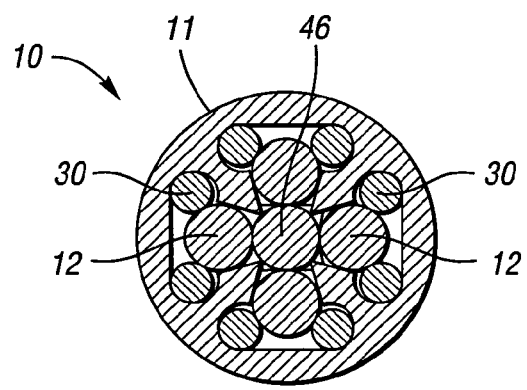
FIG. 5 is a cross-sectional view of a hub of the filter in FIG. 2a taken along line 5-5.

FIG. 5 illustrates a cross-sectional view of the filter 10 of FIG. 3a at hub 11. As shown, the hub 11 houses a bundle of first ends 14 of the four primary struts 14 and connected ends 32 of secondary struts 30. FIG. 5 further depicts the configurations of the primary and secondary struts 12 and 30. In this embodiment, the primary struts 12 are spaced between two secondary struts 30. Of course, the primary struts 12 may be spaced between any other suitably desired number of secondary struts 30 without falling beyond the scope or spirit of the present invention.

Figure 6:
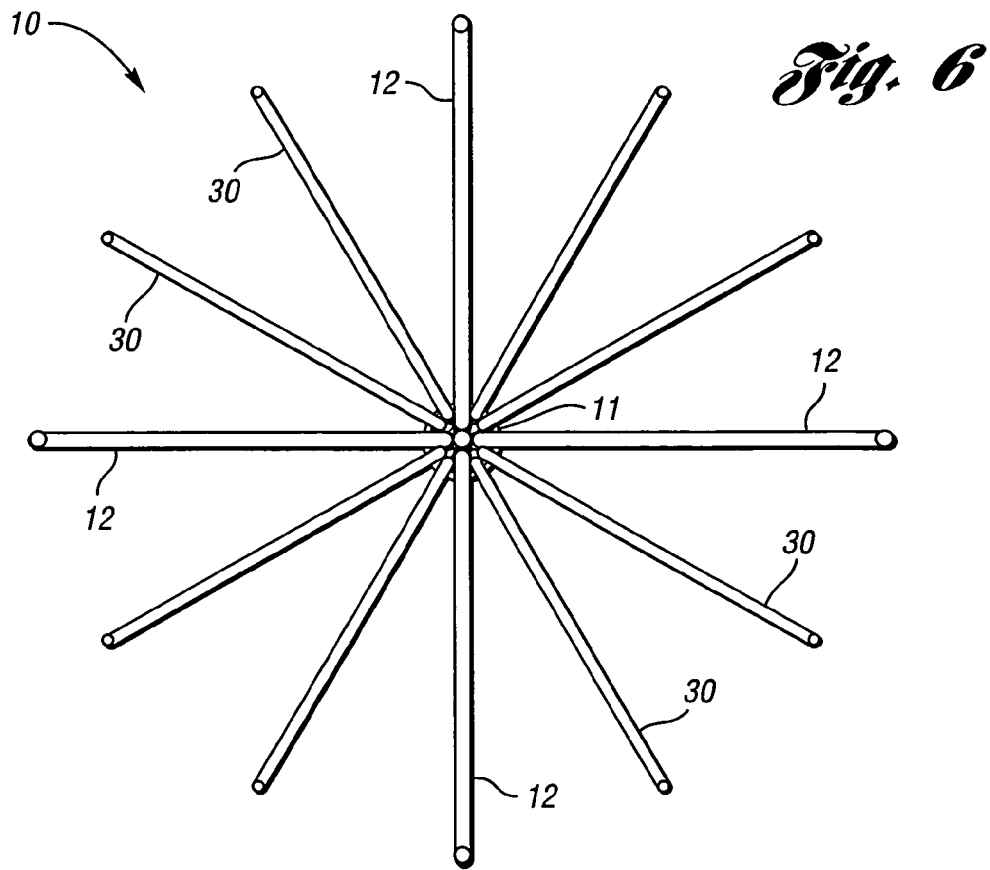
FIG. 6 is an end view of the filter of FIG. 2a taken along line 6-6.

FIG. 6 illustrates the netting pattern including primary struts and secondary struts independently spaced substantially equally at their respective planes. For example, the secondary struts 30 may be spaced equally relative to the other secondary struts 30 and the primary struts 12 may be spaced equally relative to the other primary struts 12. As a result, the netting pattern in this embodiment shown by the end view of the vena cava (taken along line 6-6) will have uneven or unequal spacing between the primary struts 12 and secondary struts 30. However, it is to be understood that the primary and secondary struts may be arranged in any other suitable manner as desired.

Although the embodiments of this device have been disclosed as being constructed from wire having a round cross section, it could also be cut from a tube of suitable material by laser cutting, electrical discharge machining or any other suitable process.

In the event that the filter has stayed in the vessel for a longer period of time, the primary struts may be overgrown by neovascular overgrowth of the intima layer of the vessel wall. The tendency of overgrowing of the struts is increased by the spring biased configuration of the struts and the radial outward orientation of the outer end of the struts in relation to the longitudinal axis. This results in the struts dilating the vessel wall along the contact surface of the struts with the vessel wall. The intima layer overgrowing the struts will increase the anchoring of the filter, so the struts will follow the movements of the wall, and migration of the filter is avoided. Even when the struts are overgrown by intima layer, the filter may be removed without any substantial damage to the vessel wall. The intima layer that has overgrown the struts will restrict the pulling forces to act parallel to the wall and thereby pulling the struts out easily, instead of breaking the overgrown layer. Apart from a small cut caused by the hook, there will not be any further damage and the cut will heal in relatively less time whereas tearing of the intima layer would otherwise take relatively more time to heal.

The filter 10 may be comprised of any suitable material such as superelastic material, nitinol, stainless steel wire, cobalt-chromium-nickel-molybdenum-iron alloy, or cobalt-chrome alloy. It is understood that the filter 10 may be formed of any other suitable material that will result in a self-opening or self-expanding filter, such as shape memory alloys. Shape memory alloys have a property of becoming rigid, that is, returning to a remembered state, when heated above a transition temperature. A shape memory alloy suitable for the present invention may comprise Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one alternate embodiment, the filter 10 may be made from Nitinol with a transition temperature that is slightly below normal body temperature of humans, which is about 98.6° F. Although not necessarily a preferred embodiment, when the filter 10 is deployed in a body vessel and exposed to normal body temperature, the alloy of the filter 10 will transform to austenite, that is, the remembered state, which for one embodiment of the present invention is the expanded configuration when the filter 10 is deployed in the body vessel. To remove the filter 10, the filter 10 is cooled to transform the material to martensite which is more ductile than austenite, making the filter 10 more malleable. As such, the filter 10 can be more easily collapsed and pulled into a lumen of a catheter for removal.

In another alternate embodiment, the filter 10 may be made from Nitinol with a transition temperature that is above normal body temperature of humans, which is about 98.6° F. Although not necessarily a preferred embodiment, when the filter 10 is deployed in a body vessel and exposed to normal body temperature, the filter 10 is in the martensitic state so that the filter 10 is sufficiently ductile to bend or form into a desired shape, which for the present invention is an expanded configuration. To remove the filter 10, the filter 10 is heated to transform the alloy to austenite so that the filter 10 becomes rigid and returns to a remembered state, which for the filter 10 in a collapsed configuration.

While the present invention has been described in terms of preferred embodiments, it will be understood, of course, that the invention is not limited thereto since modifications may be made to those skilled in the art, particularly in light of the foregoing teachings.

The invention claimed is:

1. A removable filter for capturing thrombi in a blood vessel, the filter comprising:
    a plurality of primary struts having first ends attached together along a longitudinal axis of the filter, the plurality of primary struts including a pair of opposed primary struts having opposed first ends relative to the longitudinal axis, each primary strut having a first length including an arcuate segment having a soft S-shape and terminating with an anchoring hook, the arcuate segment of each primary strut having a first curved portion, a second curved portion, and a third curved portion, each curved portion curving in a different direction than the other curved portions, the first curved portion of each primary strut extending from the first end of the respective primary strut radially away from the longitudinal axis and the second curved portion of each primary strut extending directly from the first curved portion of the respective primary strut radially toward the longitudinal axis to define the soft S-shape, the second curved portion terminating with the anchoring hook, the first curved portion of each primary strut including the third curved portion defined by an axial bend angled consistently from the longitudinal axis of the filter, wherein the axial bend is formed by a bend on each primary strut by between about 0.5 degree and 5 degrees at right angles relative to the first end of the respective primary strut and the longitudinal axis of the filter such that the primary struts are configured to maintain a consistent orientation when moving between expanded and collapsed states, wherein the axial bends of the opposed primary struts offset the opposed primary struts relative to one another to allow the opposed primary struts to avoid entanglement with one another when moving between the expanded and collapsed states, the primary struts being configured to move to the collapsed state for filter retrieval or delivery and the expanded state for engaging with the blood vessel; and
    a plurality of secondary struts having connected ends attached together along the longitudinal axis, each secondary strut freely extending from the connected end to a free end to centralize the filter in the expanded state in the blood vessel, each secondary strut extending arcuately along a longitudinal plane and linearly along a diametric plane from the connected end to the free end, each secondary strut having a second length including a first arc and a second arc, the first arc extending from the connected end away from the longitudinal axis and terminating at the free end without a hook.

2. The removable filter of claim 1 further comprising:
    a hub configured to axially house the first ends of the plurality of primary struts and the connected ends of the secondary struts; and
    a retrieval hook extending from the hub opposite the plurality of primary struts and the plurality of secondary struts for removal of the filter from the blood vessel.

3. The removable filter of claim 1 wherein the configuration of anchoring hooks in the expanded state defines a first axial plane and the free ends of the secondary struts in the expanded state defines a second axial plane to centralize the filter in the blood vessel.

4. The removable filter of claim 1 wherein the first and second curved portions of the primary struts are configured to have a non-parallel relationship with the longitudinal axis of the filter.

5. The removable filter of claim 1 wherein each primary strut has a diameter of at least about 0.015 inch.

6. The removable filter of claim 1 wherein each primary strut is formed of a superelastic material, nitinol, stainless steel wire, cobalt-chromium-nickel-molybdenum-iron alloy, or cobalt-chrome alloy, or a mixture thereof.

7. The removable filter of claim 1 wherein each secondary strut has a diameter of 0.012 inch.

8. The removable filter of claim 1 wherein each secondary strut is formed of a superelastic material, nitinol, stainless steel wire, cobalt-chromium-nickel-molybdenum-iron alloy, or cobalt-chrome alloy, or a mixture thereof.

9. The removable filter of claim 1 wherein the primary struts and the secondary struts expand to a diameter of between about 25 and 45 millimeters.

10. The removable filter of claim 9 wherein the length of each primary strut is about 5 centimeters.

11. The removable filter of claim 10 wherein the primary struts are configured to pivot at the first ends thereof to move between the collapsed and expanded configurations.

12. The removable filter of claim 1 wherein the primary struts and the secondary struts include a minimal diameter defining the collapsed configuration of the filter and a maximum diameter defining the expanded configuration of the filter.

13. A removable filter for capturing thrombi in a blood vessel, the filter comprising:

a plurality of primary struts having first ends attached together along a longitudinal axis of the filter, the plurality of primary struts including a pair of opposed primary struts having opposed first ends relative to the longitudinal axis, each primary strut including an arcuate segment having a soft S-shape and terminating with an anchoring hook, the anchoring hook being integral with the arcuate segment and having the same thickness as the arcuate segment, the arcuate segment of each primary strut having a first curved portion, a second curved portion, and a third curved portion, each curved portion curving in a different direction than the other curved portions, the first curved portion of each primary strut extending from the first end of the respective primary strut radially away from the longitudinal axis and the second curved portion of each primary strut extending directly from the first curved portion of the respective primary strut radially toward the longitudinal axis to define the soft S-shape, the second curved portion terminating with the anchoring hook, the first curved portion of each primary strut including the third curved portion defined by an axial bend angled consistently from the longitudinal axis of the filter, wherein the axial bend of each primary strut of the pair of opposed primary struts is formed by a bend on each primary strut by between about 0.5 degree and 2 degrees at right angles relative to the first end of the respective primary strut and the longitudinal axis of the filter so as to offset the primary struts of the pair of opposed primary struts relative to the longitudinal axis such that the opposed primary struts are configured to extend substantially in parallel and cooperate with one another in the collapsed state, and such that the primary struts are configured to maintain a consistent orientation when moving between expanded and collapsed states, wherein the axial bends of the opposed primary struts offset the opposed primary struts relative to one another to allow the opposed primary struts to avoid entanglement with one another when moving between the expanded and collapsed states, the primary struts being configured to move to the collapsed state for filter retrieval or delivery and the expanded state for engaging with the blood vessel.

* * * * *